United States Patent
Mauhar et al.

(10) Patent No.: US 12,357,213 B2
(45) Date of Patent: Jul. 15, 2025

(54) METHOD OF CONDUCTOR MANAGEMENT WITHIN A MEDICAL DEVICE

(71) Applicant: Greatbatch Ltd., Clarence, NY (US)

(72) Inventors: Christopher Mauhar, Maple Grove, MN (US); Hitesh Mehta, Plymouth, MN (US); Krishna Vedula, Plymouth, MN (US); Hugh D. Hestad, Edina, MN (US); Jeff Fleigle, Brooklyn Park, MN (US)

(73) Assignee: Greatbatch Ltd., Clarence, NY (US)

( * ) Notice: Subject to any disclaimer, the term of this patent is extended or adjusted under 35 U.S.C. 154(b) by 907 days.

(21) Appl. No.: 17/520,522

(22) Filed: Nov. 5, 2021

(65) Prior Publication Data

US 2022/0142542 A1    May 12, 2022

Related U.S. Application Data

(60) Provisional application No. 63/165,859, filed on Mar. 25, 2021, provisional application No. 63/110,389, filed on Nov. 6, 2020.

(51) Int. Cl.
| | |
|---|---|
| *A61B 5/259* | (2021.01) |
| *A61B 5/262* | (2021.01) |
| *A61B 5/273* | (2021.01) |
| *H02G 1/08* | (2006.01) |

(52) U.S. Cl.
CPC .............. *A61B 5/259* (2021.01); *A61B 5/262* (2021.01); *A61B 5/273* (2021.01); *H02G 1/083* (2013.01)

(58) Field of Classification Search
CPC .......... H02G 1/083; H02G 1/00; H02G 1/005; A61B 5/259; A61B 5/262; A61B 5/273
USPC ............... 174/146, 137 R, 138 R, 68.1, 68.3
See application file for complete search history.

(56) References Cited

U.S. PATENT DOCUMENTS

| | | | |
|---|---|---|---|
| 4,911,688 A | 3/1990 | Jones | |
| 6,694,609 B2 | 2/2004 | Lopata et al. | |
| 6,722,896 B2 | 4/2004 | McGrath et al. | |
| 9,089,689 B2 * | 7/2015 | Govea | A61N 1/05 |
| 9,386,684 B2 | 7/2016 | Sime et al. | |
| 10,709,886 B2 * | 7/2020 | Nagaoka | A61N 1/0558 |
| 11,311,719 B2 * | 4/2022 | Dubuclet | A61N 1/0556 |

FOREIGN PATENT DOCUMENTS

| | | |
|---|---|---|
| CN | 107025954 B | 6/2019 |
| DE | 102004042751 A1 | 3/2006 |
| DE | 102012112640 A1 | 6/2014 |
| WO | 9000418 A1 | 1/1990 |

* cited by examiner

*Primary Examiner* — Angel R Estrada
(74) *Attorney, Agent, or Firm* — Michael P. Horvath

(57) ABSTRACT

In various examples, a method of conductor management within a medical device includes providing a flexible substrate. The flexible substrate includes at least one routing feature. A hole is cut in the at least one routing feature with a cutting device. A conductor is passed through the hole in the at least one routing feature. The routing feature acts to maintain and manage positioning of the conductor within the medical device. The medical device, in some examples, includes a lead, with the conductor connected to an electrode of the lead after being routed through the routing feature.

20 Claims, 12 Drawing Sheets

METHOD OF CONDUCTOR MANAGEMENT WITHIN A MEDICAL DEVICE

CROSS REFERENCE TO RELATED APPLICATIONS

This application claims the benefit of priority to U.S. Provisional Application Ser. No. 63/110,389, filed on Nov. 6, 2020, entitled "CONDUCTOR MANAGEMENT BY MEANS OF FLEXIBLE SUBSTRATE SEWING," and U.S. Provisional Application Ser. No. 63/165,859, filed on Mar. 25, 2021, entitled "CONDUCTOR MANAGEMENT BY MEANS OF FLEXIBLE SUBSTRATE SEWING," each of which is incorporated by reference herein in its entirety.

BACKGROUND

Conductor management within a body of a medical device is desirable so that conductors are properly located within the often-narrow confines within the body of the medical device. Proper conductor management is also desirable to allow for proper routing within the body of the medical device and connection of conductors to components within the medical device. Typical conductor management in medical devices includes one or more of additional and separate components having preformed shapes for mechanical affixment (such as, for instance, wire channels), adhesives, clips, and/or the like. Wire channels require additional componentry to be supplied and inserted within the medical device, thereby increasing cost and manufacturing time for the medical device. Adhesives require additional materials that may include volatile organic compounds (VOCs) or other hazardous carrier fluids or materials. Adhesives can also require additional energy or processing to cure (heat, ultraviolet light, moisture, etc.), which could strain other components or require additional tooling, thereby increasing cost and manufacturing time for the medical device. Clips generally have limited application due to size limitations. Moreover, clips also require additional componentry to be supplied and inserted within the medical device, thereby increasing cost and manufacturing time for the medical device. What is desired is a method of conductor management within a medical device that does not increase componentry, introduce potentially hazardous materials to the medical device, or require additional energy or processing.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present inventive subject matter can be used to provide conductor management within a medical device without increasing componentry, introducing potentially hazardous materials to the medical device, or requiring additional energy or processing. In various examples, the present inventive subject matter is advantageous in that it provides for conductor management without requiring additional components or bulk (adhesive, clips, coatings, etc.) in order to fasten, route, and/or otherwise position conductors within the medical device. In some examples, the present inventive subject matter advantageously provides for securing of conductors within the medical device regardless of insulation material type, finish, and/or thickness of the conductors. In some examples, the present inventive subject matter is advantageous in that it allows for physical landmarks to be placed onto a flexible substrate to guide the manufacturing process for repeatability, thereby decreasing, if not eliminating, the need for measuring locations of securing points and the possibility of misaligned securing points. To better illustrate the devices and methods described herein, a non-limiting list of examples is provided here:

Example 1 can include subject matter that can include a method of conductor management within a medical device. The method includes providing a flexible substrate, the flexible substrate including at least one routing feature. With a cutting device, a hole is cut in the at least one routing feature. A conductor is passed through the hole in the at least one routing feature, the routing feature acting to maintain and manage positioning of the conductor within the medical device.

In Example 2, the subject matter of Example 1 is optionally configured such that cutting the hole includes piercing the hole through the at least one routing feature using a needle.

In Example 3, the subject matter of Example 2 is optionally configured such that passing the conductor through the hole includes threading the conductor through a lumen of the needle with the needle disposed within the hole and removing the needle from within the hole and over the conductor to leave the conductor within the hole of the at least one routing feature.

In Example 4, the subject matter of any one of Examples 1-3 is optionally configured such that cutting the hole includes cutting the hole through the at least one routing feature using a blade.

In Example 5, the subject matter of any one of Examples 1-4 optionally includes encapsulating the flexible substrate with the conductor disposed within the hole in the at least one routing feature to completely encase the conductor.

In Example 6, the subject matter of any one of Examples 1-5 optionally includes attaching the conductor to an electrode disposed within the flexible substrate.

In Example 7, the subject matter of any one of Examples 1-6 is optionally configured such that providing the flexible substrate includes the flexible substrate including two or more routing features disposed along the flexible substrate.

In Example 8, the subject matter of Example 7 is optionally configured such that cutting the hole in the at least one routing feature includes cutting a hole in each of the two or more routing features.

In Example 9, the subject matter of Example 8 is optionally configured such that passing the conductor through the hole in the at least one routing feature includes passing two or more conductors through the holes in the two or more routing features.

In Example 10, the subject matter of Example 9 is optionally configured such that passing the conductor through the hole in the at least one routing feature includes passing multiple conductors of the two or more conductors through at least one of the holes in the two or more routing features.

In Example 11, the subject matter of Example 9 is optionally configured such that passing the conductor through the hole in the at least one routing feature includes passing no more than one conductor of the two or more conductors through each of the holes in the two or more routing features.

In Example 12, the subject matter of any one of Examples 1-11 is optionally configured such that providing the flexible substrate includes providing the flexible substrate with the at least one routing feature being integrally formed with the flexible substrate.

Example 13 can include, or can optionally be combined with any one of Examples 1-12 to include subject matter that can include a method of conductor management within a medical device. The method includes providing a flexible substrate, the flexible substrate including a plurality of routing features disposed along the flexible substrate. With a cutting device, a hole is cut in each of the plurality of routing features. A plurality of conductors is passed through the holes in the plurality of routing features, the plurality of routing features acting to maintain and manage positioning of the plurality of conductors within the medical device.

In Example 14, the subject matter of Example 13 is optionally configured such that cutting the hole includes piercing the hole through at least one of the plurality of routing features using a needle. Passing one of the plurality of conductors through at least one of the holes includes threading the conductor through a lumen of the needle with the needle disposed within the hole and removing the needle from within the hole and over the conductor to leave the conductor within the at least one hole.

In Example 15, the subject matter of Example 13 or 14 is optionally configured such that cutting the hole includes cutting the hole through at least one of the plurality of routing features using a blade.

In Example 16, the subject matter of any one of Examples 13-15 optionally includes encapsulating the flexible substrate with the plurality of conductors disposed within the holes in the plurality of routing features to completely encase the plurality of conductors.

In Example 17, the subject matter of any one of Examples 13-16 optionally includes attaching the plurality of conductors to a plurality of electrodes disposed within the flexible substrate.

In Example 18, the subject matter of any one of Examples 13-17 is optionally configured such that passing the plurality of conductors through the holes in the plurality of routing features includes passing multiple conductors of the plurality of conductors through at least one of the holes in the plurality of routing features.

In Example 19, the subject matter of any one of Examples 13-18 is optionally configured such that passing the plurality of conductors through the holes in the plurality of routing features includes passing no more than one conductor of the plurality of conductors through each of the holes in the plurality of routing features.

Example 20 can include, or can optionally be combined with any one of Examples 1-19 to include subject matter that can include a method of conductor management within a medical device. The method includes providing a flexible substrate, the flexible substrate including a plurality of routing features disposed along the flexible substrate. The plurality of routing features are integrally formed with the flexible substrate. With a cutting device, a hole is cut in each of the plurality of routing features. A plurality of conductors is passed through the holes in the plurality of routing features, the plurality of routing features acting to maintain and manage positioning of the plurality of conductors within the medical device. The plurality of conductors is attached to a plurality of electrodes disposed within the flexible substrate. The flexible substrate is encapsulated with the plurality of conductors disposed within the holes in the plurality of routing features to completely encase the plurality of conductors.

DETAILED DESCRIPTION

Figure 1A:
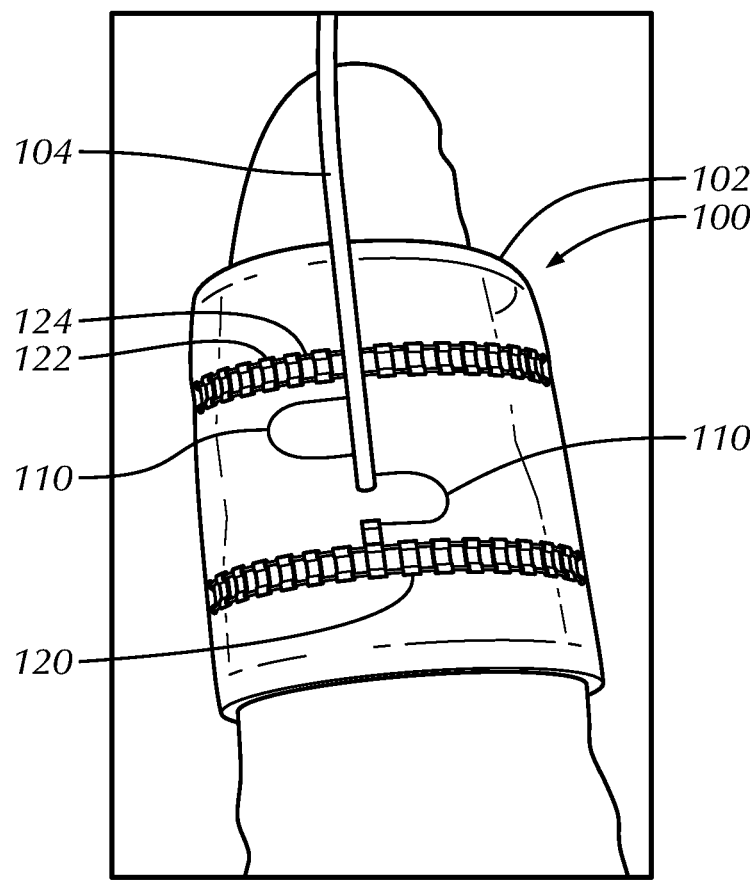
FIGS. 1A and 1B are perspective views of a medical device made using a conductor management method in accordance with at least one example of the invention.

The present inventive subject matter relates generally to providing conductor management within a medical device and/or a medical device including such conductor management. In some examples, the present inventive subject matter provides a method of conductor management without increasing componentry, introducing potentially hazardous materials to the medical device, or requiring additional energy or processing. More specifically, the present inventive subject matter can be used to provide conductor management within a medical device by forming a substrate with one or more routing features formed thereon, the one or more routing features being cut to form a hole with one or more conductors being routed through the hole in each of the one or more routing features. The present inventive subject matter, in various examples, can be used in various medical devices and/or medical device components. For instance, in some examples, the conductor management methods of the present inventive subject matter can be used in a lead of a medical device. In some examples, the present inventive subject matter can be used to provide conductor management within a lead configured for stimulation of tissue, sensing of a physiological parameter, or the like. In some examples, the present inventive subject matter can be used to provide conductor management within various types of leads, including, but not limited to paddle leads, cuff leads, and cylindrical leads. In some examples, the conductor management methods of the present inventive subject matter can be used in other medical devices, such as, but not limited to, catheters, introducers, sheathes, probes, guidewires, delivery systems, embolic protection devices, and the like.

In some examples, the present inventive subject matter allows for visual conductor organization to provide a repeatable shape for conductor strain relief and production uniformity. Moreover, in some examples, the present inventive subject matter provides physical separation and control of conductors to increase isolation and decrease potential for current leakage across channels. Additionally, the present inventive subject matter allows for planned placement and secure affixment of conductors within a medical device, which maintains positioning of the conductors within the medical device during subsequent processing, such as, but not limited to, handling, potting, reflowing, laminating, overmolding, backfilling, encapsulation, and/or other post processing steps.

In some examples, the present inventive subject matter does not require additional components or bulk, such as adhesive, clips, coatings, or the like in order to fasten conductors within the medical device. Moreover, in some examples, the conductors can be secured regardless of insulation material type, finish, or thickness. In some examples, conductors may not be compatible with other known techniques of maintaining positioning of conductors within the medical device. For instance, fluoropolymers like ethylene tetrafluoroethylene (ETFE) cannot be easily bonded with adhesive. However, the present inventive subject matter is not limited by such issues and can be used with conductors of any insulation material type, finish, or thickness.

In some examples, the present inventive subject matter allows for physical landmarks to be placed onto the flexible substrate in order to guide the manufacturing process for repeatability. In some examples, this reduces, if not eliminates, the need for measuring locations and securements of the one or more conductors. Additionally, physical landmarks can reduce, if not eliminate, misaligned securing points of the one or more conductors.

Figure 1B:
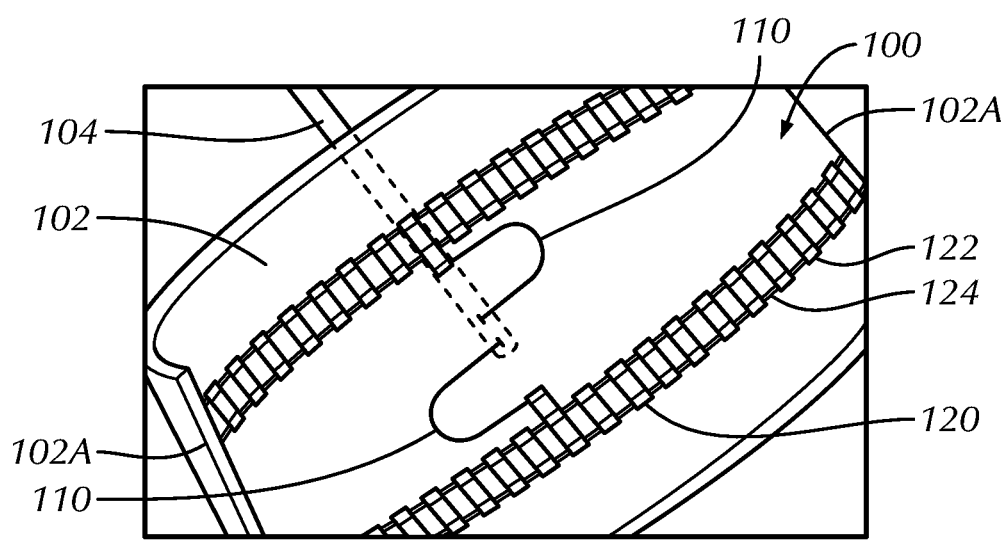

Referring to FIGS. 1A and 1B, in some examples, the present inventive subject matter can be used within a medical device 100, such as a cuff lead 100. The cuff lead 100, in some examples, includes a cuff 102 configured to form a generally round or cylindrical shape in order to wrap around a structure (FIG. 1A). In some examples, the cuff 102 can be opened (FIG. 1B) to allow the cuff 102 to be placed around the structure. In some examples, a physician or other user can separate ends 102A of the cuff 102 to allow access to an interior of the cuff 102. Once the cuff 102 is in position with respect to the structure, in some examples, the cuff 102 can be released to wrap around the structure (FIG. 1A). In this way, in some examples, one or more electrodes 122 of the cuff lead 100 can be positioned proximate the structure in order to electrically stimulate the structure, measure properties of the structure, or the like. In some examples, the cuff lead 100 includes one or more electrode strips 120 disposed within the cuff 102, each electrode strip 120 including two or more electrodes 122 electrically coupled together using electrode wires 124. In some examples, the electrode wires 124 can be pre-formed into a generally circular form to give the cuff 102 its generally round or cylindrical shape but also allow the cuff 102 to be opened by spreading apart the ends 102A of the cuff 102. In some examples, the one or more electrodes 122 are exposed or extend at least slightly out of an interior surface of the cuff 102 to allow the one or more electrodes 122 to directly contact the structure around which the cuff 102 is placed to allow for proper electrical stimulation of the structure, property measurement of the structure, or the like. In some examples, the one or more electrode strips 120 are electrically coupled to one or more conductors 110, which, in turn, extend proximally into and through a lead wire 104 to a proximal device. The proximal device, in various examples, can include different types of devices, including, but not limited to, one or more of an implanted device, an external device, a stimulation device, a monitoring device, a drug-dispensing device, or the like.

In some examples, proper routing of the one or more conductors 110 within the cuff 102 is important to allow for proper electrical connections; inhibition, if not elimination, of potential electrical shorting; and proper layout and positioning of the one or more conductors 110 given the performance requirements of the cuff lead 100. In order to obtain such proper routing of the one or more conductors 110, in some examples, the one or more conductors 110 must be placed and maintained in the proper positions throughout formation and manufacture of the cuff lead 100. Various methods of conductor 110 management are described herein with respect to various medical devices, such as the cuff lead 100.

Referring now to FIGS. 2A-2D, in some examples, a method of conductor 110 management for a medical device, such as the cuff lead 100, is shown. In some examples, a flexible substrate 130 is provided, the flexible substrate 130 including at least one routing feature 140. The flexible substrate 130 can include the at least one electrode strip 120 disposed therein and/or thereon. The at least one electrode strip 120, in some examples, is located along the flexible substrate 130 in a proper position for the cuff lead 100. In some examples, the at least one electrode strip 120 includes an electrode connector 126 configured to allow electrical connection of the electrodes 122 of the at least one electrode strip 120 to the at least one conductor 110. In some examples, the at least one conductor 110 is engaged with the electrode connector 126, for instance, the at least one conductor 110 being one or more of crimped, welded, brazed, soldered, or the like to the electrode connector 126.

In some examples, the at least one routing feature 140 is configured to anchor, route, and/or otherwise position the at least one conductor 110 within the cuff 102 of the cuff lead 100. In some examples, the at least one routing feature 140 is integrally formed with the flexible substrate 130. In some examples, the at least one routing feature 140 includes a raised feature 142 extending from a surface of the flexible substrate 130. In various examples, the raised feature 142 can include one or more of a rib, a bump, a protrusion, or the like, extending outwardly from the surface of the flexible substrate 130. In some examples, the at least one routing feature 140 can include two raised features 142, for instance, to anchor, hold, or otherwise constrain two conductors 110. In still other examples, the substrate can include at least one routing feature with more than two raised features and/or more than one routing feature, depending upon the number of conductors that are to be used within the cuff lead. In such instances, the present method of conductor 110 management for a medical device, such as the cuff lead 100, can be repeated for each conductor 110 that is to be used within the cuff lead 100. For the sake of simplicity, the present method of conductor 110 management for a medical device, such as the cuff lead 100, is described for only the one conductor 110 shown in FIGS. 2A-2D.

Initially, in some examples, the present method of conductor 110 management includes identifying the one or more routing features 140 on the flexible substrate 130 and understanding a planned conductor 110 arrangement, for instance, as detailed in a manufacturing procedure.

Figure 2A:
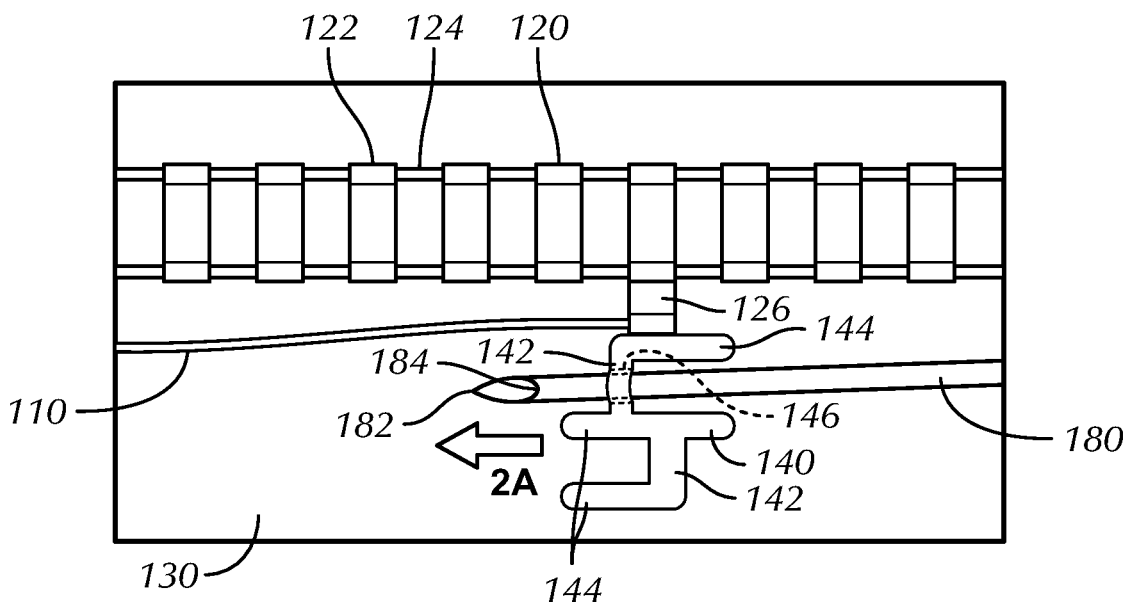
FIGS. 2A-2D are perspective views of steps of a conductor management method in accordance with at least one example of the invention.

Referring now to FIG. 2A, in some examples, a hole 146 is cut in the at least one routing feature 140 using a cutting device 180. In some examples, this is performed once the at least one electrode strip 120 is properly positioned with respect to the flexible substrate 130 with the at least one conductor 110 being engaged and electrically coupled to the electrode connector 126. However, in other examples, the hole 146 is cut in the at least one routing feature 140 prior to placement and/or positioning of the at least one electrode strip 120 with respect to the flexible substrate 130 and/or prior to engagement and electrically coupling of the at least one conductor 110 to the electrode connector 126. In some examples, the cutting device 180 includes a needle 180, such as, for instance, a hypodermic needle. In some examples, the needle 180 includes a 12-degree bevel pointed hypodermic needle. In some examples, the needle 180 includes a distal tip 182 configured to enable piercing of the at least one routing feature 140. In further examples, the distal tip 182 can include a sharpened tip to facilitate piercing of the at least one routing feature 140 with the needle 180. In some examples, the needle 180 includes a lumen 184, open at the distal tip 182 of the needle 182 and extending through a length of the needle 180. In some examples, the needle 180 is sized to allow passage of the conductor 110 within the lumen 184 of the needle 180. In some examples, the needle 180 is pushed through the raised feature 142 along arrow 2A. That is, in some examples, a user places the needle 180 at one side of the raised feature 142 and pushes the needle 180 along the arrow 2A through the raised feature 142 and out through the other side of the raised feature 142 to create the hole 146 through the raised feature 142. Although the cutting device 180 is described in some examples as being a needle 180, in other examples, other cutting devices can be used to form the hole 146 in the at least one routing feature 140, such as, but not limited to, a blade, a drill, a poker, a heated probe, a laser, and/or the like. In some examples, the hole 146 is disposed within the raised feature 142 in an intermediate portion of the raised feature 142 between the flexible substrate 130 and a top of the raised portion 142, such that there is material of the raised feature 142 both above and below the hole 146. In other examples, the hole can be formed at the top of the raised feature, such that the hole forms essentially a notch in the top of the raised feature. In still other examples, the hole can be formed at a bottom of the raised feature where the raised feature meets the flexible substrate.

In some examples, the at least one routing feature 140 includes at least one guide feature 144 configured to guide placement and/or positioning of the needle 180 and, in turn, ultimately the placement and/or positioning of the conductor 110 with respect to the at least one routing feature 140. In the example shown in FIG. 2A, the at least one routing feature 140 includes two guide features 144 associated with the raised feature 142, wherein the guide features 144 are substantially parallel to each other, are substantially perpendicular to the raised feature 142, and extend in the same direction from the raised feature 142 to form a generally U-shaped form to help guide the user when positioning the needle 180. In this way, in some examples, the user positions the distal tip 182 of the needle 180 in between and generally parallel with the guide features 144 to properly place the needle 180 prior to piercing the raised feature 142 in order to ensure that the raised feature 142 is properly pierced. It is noted that in the example shown in FIG. 2A, there is a second raised feature 142 and a third guiding feature 144 to allow for guiding of the needle 180 and piercing of the other raised feature 142 for a second conductor. As stated above, the present method of conductor 110 management for a medical device, such as the cuff lead 100, can be repeated for each raised feature 142 and/or each conductor 110 as is necessary in order to properly route each of the conductors 110 within the cuff 102 of the cuff lead 100.

Figure 2B:
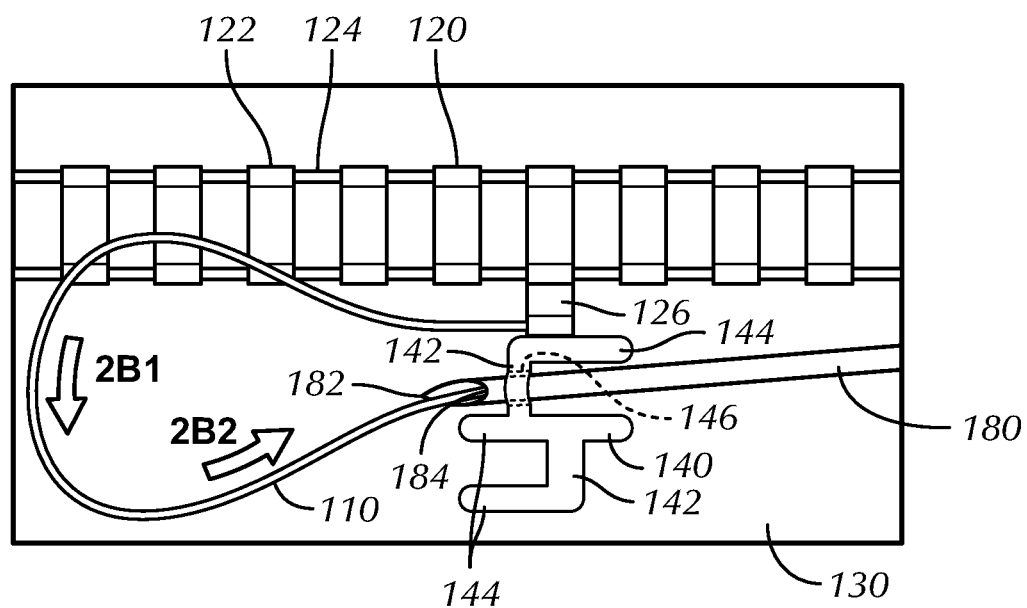

Referring now to FIG. 2B, in some examples, once the hole 146 is formed in the raised feature 142 of the at least one routing feature 140, the conductor 110 is passed through the hole 146 in order to at least partially constrain the conductor 110, thereby maintaining the orientation and position of the conductor 110 with respect to the at least one routing feature 140 and the flexible substrate 130. In this way, in some examples, the routing feature 140 acts to maintain and manage positioning of the conductor 110 within the medical device, such as, for instance, the cuff lead 100. In some examples, once the needle 180 is pierced through the raised feature 142, the needle 180 is momentarily left within the hole 146 in the raised feature 142, such that an end of the conductor 110 can be directed along arrows 2B1, 2B2 to be threaded into the lumen 184 of the needle 180 in order to pass the conductor 110 into and through the hole 146 in the raised feature 142 of the at least one routing feature 140. In some examples, once the conductor 110 is threaded through the lumen 184 of the needle 180, the needle 180 can be removed from within the hole 146 and over the conductor 110 to leave the conductor 110 within the hole 146 of the raised feature 142 of the at least one routing feature 140. In this way, the needle 180 can then be used to pierce another raised feature 142 to route another conductor 110 or further route the same conductor 110, depending upon the configuration of the one or more electrode strips 120 and/or one or more conductors 110, or the needle 180 can be removed to allow for further processing of the cuff 102 and the cuff lead 100.

Figure 2C:
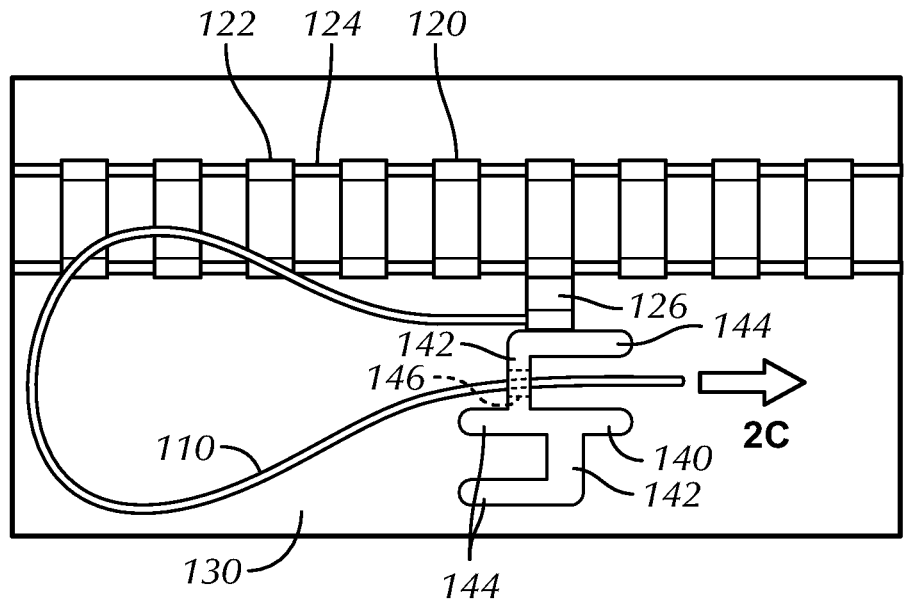
Figure 2D:
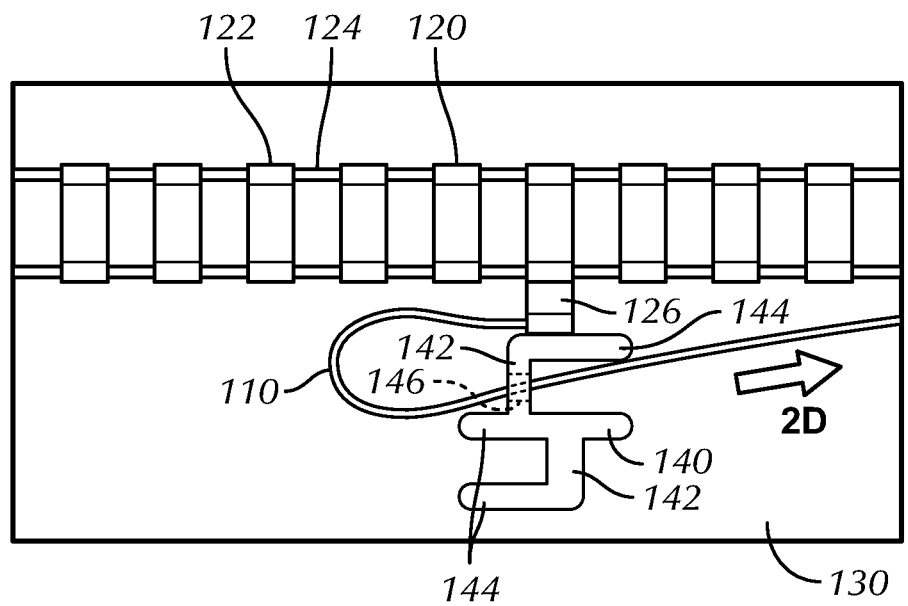

Referring now to FIGS. 2C and 2D, once the needle 180 is removed from within the hole 146 and the conductor 110, the conductor 110 can be further pulled through the hole 146 along arrows 2C, 2D in order to place the conductor in the desired position, location, and/or orientation. In the present example, the conductor 110 is pulled through the hole 146 in the raised feature 142 of the routing feature 140 such that the conductor 110 includes a slight bend between the electrode connector 126 and the hole 146 in the at least one routing feature 140 and extends from the hole 146 sufficiently to allow for further processing of the cuff lead 100. In this way, in some examples, the conductor 110 is routed to minimize, if not eliminate, stress concentrations, kink points, and other conditions detrimental to performance of the conductor 110 and, in turn, the cuff lead 100, during a service life of the cuff lead 100. Also, in some examples, the conductor 110 can be maintained away from other structures of the cuff lead 100, such as, for instance, other conductors and/or the one or more electrode strips 120, to decrease a chance of shorting between other structures and the conductor 110.

As discussed above, the present method of conductor 110 management for a medical device, such as the cuff lead 100, is repeated for each conductor 110 of the cuff lead 100 until each conductor 110 is properly oriented, located, or otherwise positioned. In the present example, the cuff lead 100 includes two conductors 110, so, once both conductors 110 are properly oriented, located, or otherwise positioned with respect to the flexible substrate 130, the electrode strips 120, and each other, with the conductors 110 being maintained in place and constrained by being passed through the holes 146 in the raised features 142, further processing of the cuff lead 100 can be performed. In some examples, once all of the one or more conductors 110 are routed through the proper routing features 140, any necessary final adjustments are made to finalize shape, spacing, positioning, location, and/or orientation of the one or more conductors 110. Such shape, spacing, positioning, location, and/or orientation of the one or more conductors 110 is maintained by the constraint offered by the at least one or more conductors 110 being routed through the one or more holes 146 in the one or more raised features 142 of the one or more routing features 140.

Referring again to FIGS. 1A and 1B, in some examples, once the at least one conductor 110 is properly routed and constrained with respect to the flexible substrate 130, the flexible substrate 130 is encapsulated with the at least one conductor 110 disposed within the hole 146 in the at least one routing feature 140 to completely encase the at least one conductor 110. Such encapsulation, in various examples, can include various additional processing, such as, but not limited to, overmolding, backfilling, potting, reflowing, and/or laminating. In some examples, such additional processing forms the cuff 102 and encapsulates the one or more conductors 110 within the cuff 102 in the proper shape, spacing, positioning, location, and/or orientation that was maintained during encapsulation and any additional processing using the one or more routing features 140, as described herein. In some examples, the material used for encapsulation is the same as the material of the flexible substrate 130. In other examples, the encapsulation material is different than the flexible substrate 130 material. In some examples, the one or more conductors 110 extend from the cuff 102 through the lead wire 104 for connection to a device (such as a stimulation, monitoring, and/or other device) at the proximal end of the lead wire 104.

Figure 3:
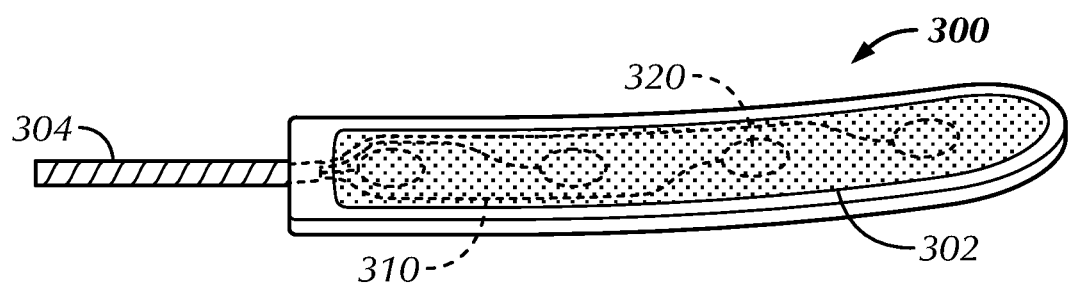
FIG. 3 is a perspective view of a medical device made using a conductor management method in accordance with at least one example of the invention.

Referring to FIG. 3, in some examples, the present inventive subject matter can be used within a medical device 300, such as a paddle lead 300. The paddle lead 300, in some examples, includes a paddle 302 at a distal end of the paddle lead 300, the paddle 302 being configured to be implanted within a patient for stimulation of tissue or other structures within the patient and/or monitoring of physiological parameters. In some examples, the paddle 302 includes one or more electrodes 320 to be positioned proximate the tissue or other structure in order to electrically stimulate the structure, measure properties of the structure, or the like. In some examples, the one or more electrodes 320 are exposed or extend at least slightly out of a surface of the paddle 302 to allow the one or more electrodes 320 to directly contact the tissue or other structure against which the paddle 302 is placed to allow for proper electrical stimulation of the tissue or other structure, physiological parameter measurement of the tissue or other structure, or the like. In some examples, the one or more electrodes 320 are electrically coupled to one or more conductors 310, which extend proximally into and through a lead wire 304 to a proximal device. The proximal device, in various examples, can include different types of devices, including, but not limited to, one or more of an implanted device, an external device, a stimulation device, a monitoring device, a drug-dispensing device, or the like.

In some examples, proper routing of the one or more conductors 310 within the paddle 302 is important to allow for proper electrical connections; inhibition, if not elimination, of potential electrical shorting; and proper layout and positioning of the one or more conductors 310 given the performance requirements of the paddle lead 300. In order to obtain such proper routing of the one or more conductors 310, in some examples, the one or more conductors 310 must be placed and maintained in the proper positions throughout formation and manufacture of the paddle lead 300. Various methods of conductor 310 management are described herein with respect to various medical devices, such as the paddle lead 300.

Initially, in some examples, the present method of conductor 310 management includes identifying the one or more routing features 340 on the flexible substrate 330 and understanding a planned conductor 310 arrangement, for instance, as detailed in a manufacturing procedure.

Referring now to FIGS. 4A-4F, in some examples, a method of conductor 310 management for a medical device, such as the paddle lead 300, is shown. In some examples, a flexible substrate 330 is provided, the flexible substrate 330 including at least one routing feature 340. The flexible substrate 330 can include the at least one electrode 320 disposed therein and/or thereon. In some examples, the flexible substrate 330 include at least one void 332 therein configured to accept the at least one electrode 320 within the void 332 when the at least one electrode 320 is to be affixed within the flexible substrate 330. The at least one electrode 320, in some examples, is located along the flexible substrate 330 in a proper position for the paddle lead 300 to allow the at least one electrode 320 to perform to electrically stimulate the tissue or other structure, measure the physiological parameter of the tissue or other structure, or the like.

In some examples, the at least one routing feature 340 is configured to anchor, route, and/or otherwise position the at least one conductor 310 within the paddle 302 of the paddle lead 300. In some examples, the at least one routing feature 340 is integrally formed with the flexible substrate 330. In some examples, the at least one routing feature 340 extends outwardly from a surface of the flexible substrate 330. In various examples, the routing feature 340 can include one or more of a rib, a bump, a protrusion, or the like, extending outwardly from the surface of the flexible substrate 330. In some examples, the flexible substrate 330 can include more than one routing feature 340, depending upon the number of conductors 310 that are to be used within the paddle lead 300 and the intended routing of the conductors 310 within the paddle 302. In such instances, the present method of conductor 310 management for a medical device, such as the paddle lead 300, can be repeated for each conductor 310 that is to be used within the paddle lead 300.

Figure 4A:
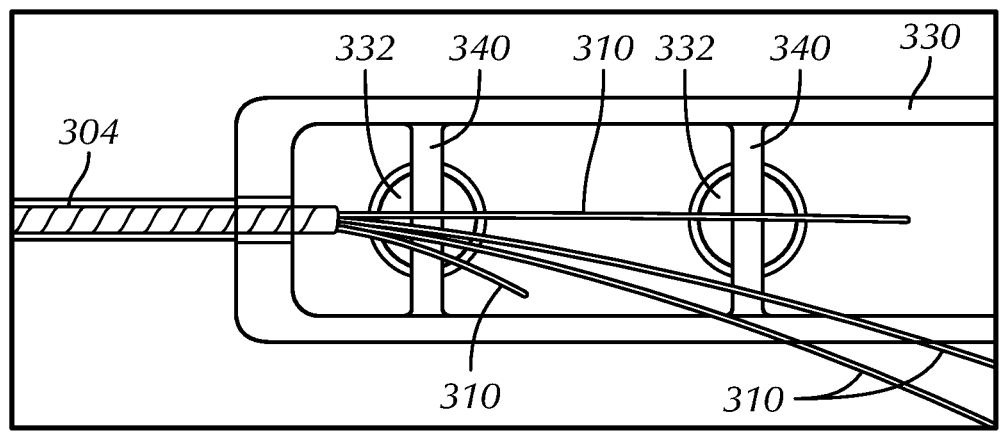
FIGS. 4A-4F are perspective views of steps of a conductor management method in accordance with at least one example of the invention.
Figure 4B:
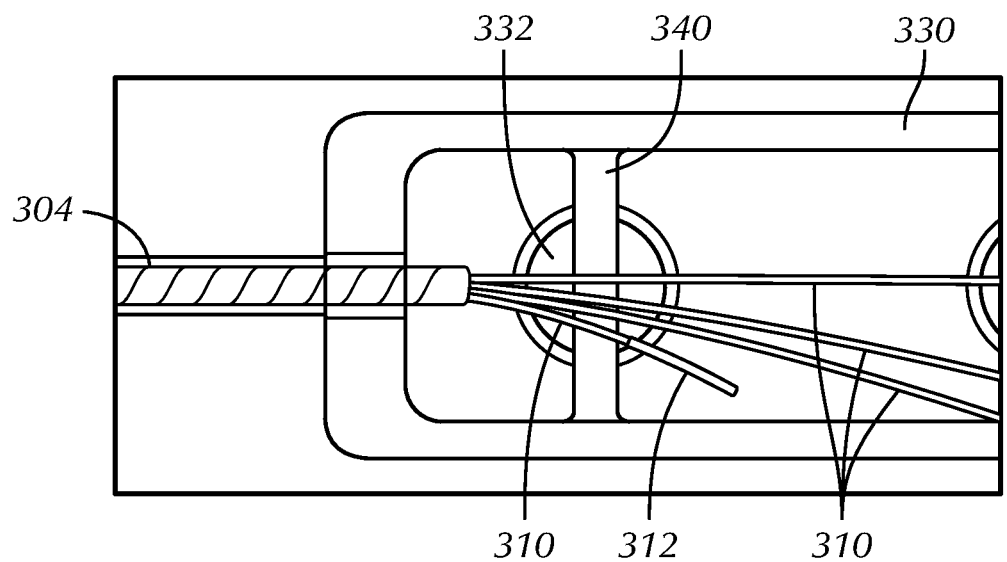

Referring now to FIGS. 4A and 4B, in some examples, one or more conductors 310 extend distally from within the lead wire 304 toward the flexible substrate 330 attached to a distal end of the lead wire 304. In the example shown in FIGS. 4A and 4B, there are four conductors 310 extending from within the lead wire 304. However, this is not intended to be limiting. As such, in other examples, there can be more or fewer than four conductors, depending upon the number of electrodes associated with the paddle lead and the purpose or function of the paddle lead. In some examples, the one or more conductors 310 can include coil or straight cable. In some examples, the one or more conductors 310 include a crimp tube 312 at the end of each of the one or more conductors 310 (FIG. 4B). In other examples, the one or more conductors 310 do not include a crimp tube (FIG. 4A).

Figure 4C:
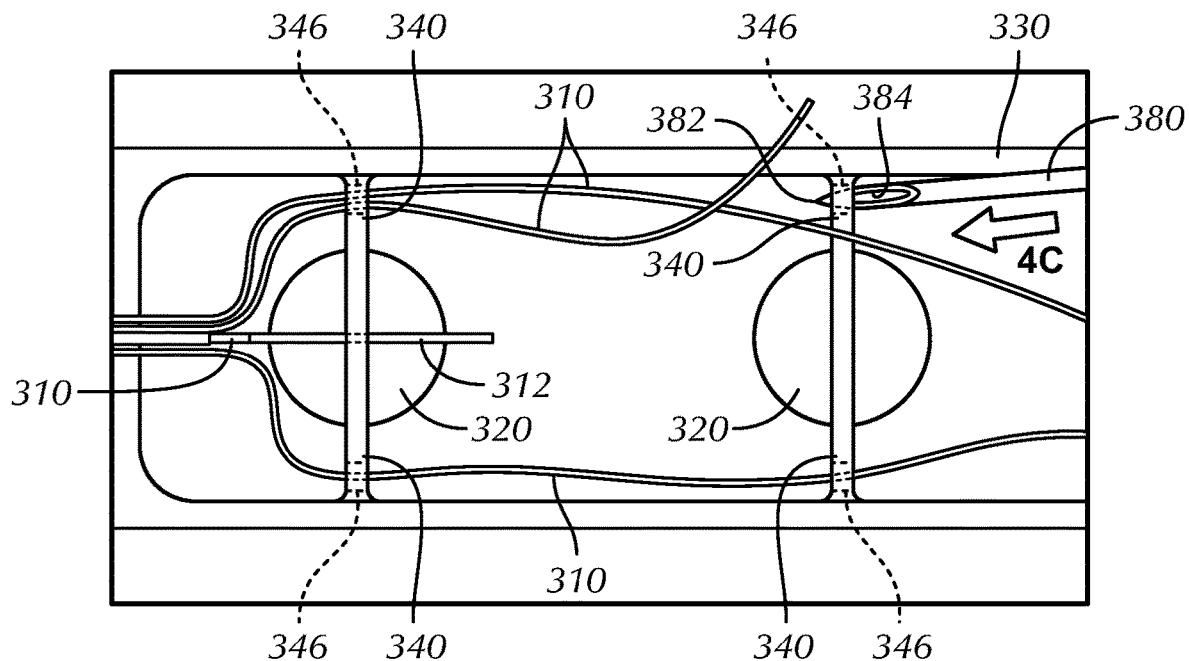

Referring to FIG. 4C, in some examples, a hole 346 is cut in the at least one routing feature 340 using a cutting device 380. In some examples, the cutting device 380 includes a needle 380, such as, for instance, a hypodermic needle. In some examples, the needle 380 includes a 12-degree bevel pointed hypodermic needle. In some examples, the needle 380 includes a distal tip 382 configured to enable piercing of the at least one routing feature 340. In further examples, the distal tip 382 can include a sharpened tip to facilitate piercing of the at least one routing feature 340 with the needle 380. In some examples, the needle 380 includes a lumen 384, open at the distal tip 382 of the needle 380 and extending through a length of the needle 380. In some examples, the needle 380 is sized to allow passage of the conductor 310 within the lumen 384 of the needle 380. In some examples, the needle 380 is pushed through the routing feature 340 along arrow 4C. That is, in some examples, a user places the needle 380 at one side of the routing feature 340 and pushes the needle 380 along the arrow 4C through the routing feature 340 and out through the other side of the routing feature 340 to create the hole 346 through the routing feature 340. Although the cutting device 380 is described in some examples as being a needle 380, in other examples, other cutting devices can be used to form the hole 346 in the at least one routing feature 340, such as, but not limited to, a blade, a drill, a poker, a heated probe, a laser, and/or the like. In some examples, the hole 346 is disposed within the routing feature 340 in an intermediate portion of the routing feature 340 between the flexible substrate 330 and a top of the routing feature 340, such that there is material of the routing feature 340 both above and below the hole 346. In other examples, the hole can be formed at the top of the routing feature, such that the hole forms essentially a notch in the top of the routing feature. In still other examples, the hole can be formed at a bottom of the routing feature where the routing feature meets the flexible substrate.

Figure 4D:
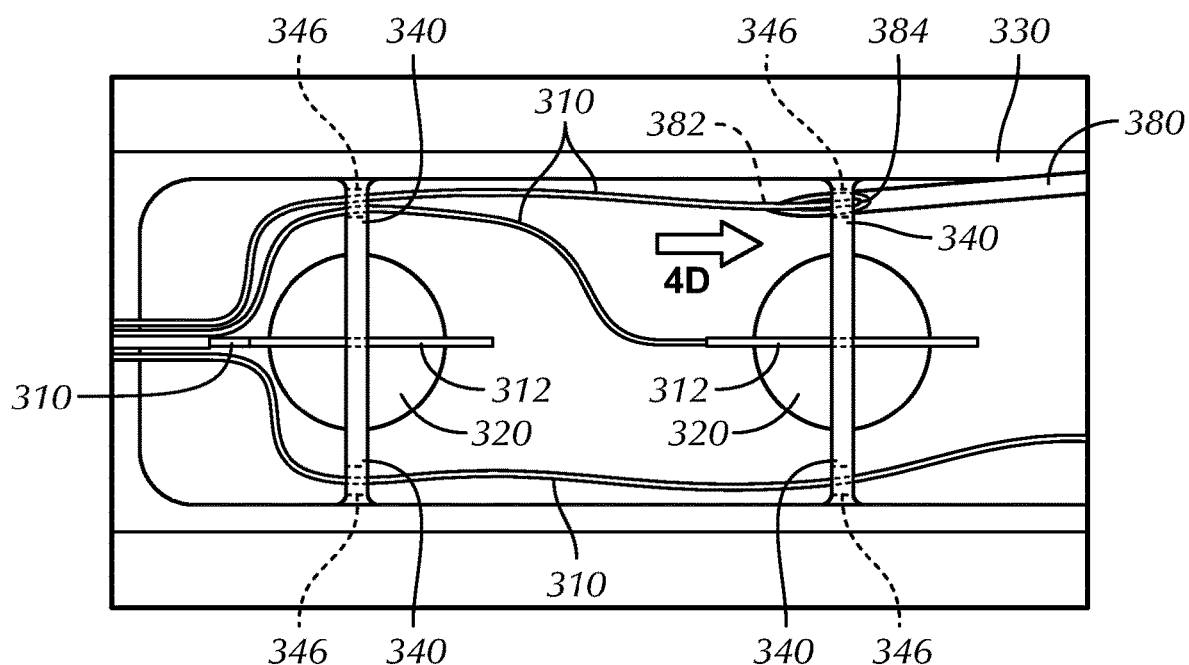

Referring now to FIG. 4D, in some examples, once the hole 346 is formed in the routing feature 340, the conductor 310 is passed through the hole 346 in order to at least partially constrain the conductor 310, thereby maintaining the orientation and position of the conductor 310 with respect to the at least one routing feature 340 and the flexible substrate 330. In this way, in some examples, the routing feature 340 acts to maintain and manage positioning of the conductor 310 within the medical device, such as, for instance, the paddle lead 300. In some examples, once the needle 380 is pierced through the routing feature 340, the needle 380 is momentarily left within the hole 346 in the routing feature 340, such that an end of the conductor 310 can be directed along arrow 4D to be threaded into the lumen 384 of the needle 380 in order to pass the conductor 310 into and through the hole 346 in the routing feature 340. In some examples, once the conductor 310 is threaded through the lumen 384 of the needle 380, the needle 380 can be removed from within the hole 346 and over the conductor 310 to leave the conductor 310 within the hole 346 of the routing feature 340. In this way, the needle 380 can then be used to pierce another routing feature 340 to route another conductor 310 or further route the same conductor 310, depending upon the configuration of the one or more electrodes 320 and/or one or more conductors 310, or the needle 380 can be removed to allow for further processing of the paddle 302 and the paddle lead 300.

Figure 4E:
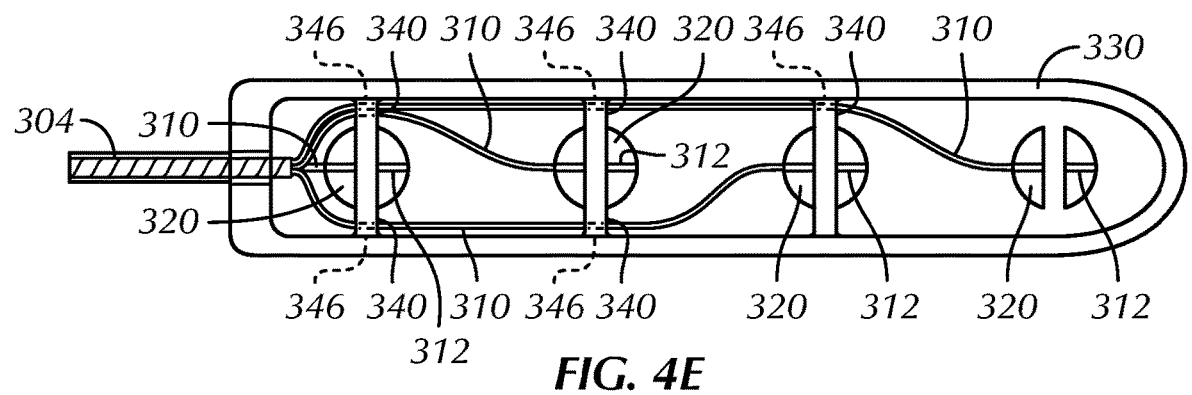

Referring now to FIG. 4E, as discussed above, the present method of conductor 310 management for a medical device, such as the paddle lead 300, is repeated for each conductor 310 of the paddle lead 300 until each conductor 310 is properly oriented, located, or otherwise positioned, using appropriate routing features 340 along a route of each conductor 310 in order to maintain such proper orientation, location, and/or positioning. In the present example, the paddle lead 300 includes four conductors 310, so, once the four conductors 310 are properly oriented, located, or otherwise positioned with respect to the flexible substrate 330, the electrodes 320, and each other, with the conductors 310 being maintained in place and constrained by being passed through the holes 346 in the routing features 340, further processing of the paddle lead 300 can be performed. In some examples, some holes 346 in some routing features 340 include more than one conductor 310 being routed therethrough in order to be routed to the proper electrode 320. In the example shown in FIG. 4E, the conductor 310 routed to the right-most electrode 320 is passed through holes 346 in upper portions (above the other electrodes 320) in the three routing features 340; the conductor 310 routed to the right-center electrode 320 is passed through holes 346 in lower portions (below the other electrodes 320) in two of the routing features 340; the conductor 310 routed to the left-center electrode 320 is passed through the hole 346 in upper portion (above the left-most electrode 320) in the left-most routing feature 340; and the conductor 310 routed to the left-most electrode 320 is passed directly from the lead wire 304. Although this conductor 310 management and routing scheme is shown in the example of FIG. 4E, it should be understood that other conductor 310 management and routing schemes can be used depending upon the size and shape of the paddle 302, the number of conductors 310, the number and placement of the electrodes 320, and the purpose and performance requirements of the paddle lead 300. In some examples, once all of the one or more conductors 310 are routed through the proper routing features 340, any necessary final adjustments are made to finalize shape, spacing, positioning, location, and/or orientation of the one or more conductors 310. Such shape, spacing, positioning, location, and/or orientation of the one or more conductors 310 is maintained by the constraint offered by the at least one or more conductors 310 being routed through the one or more holes 346 in the one or more routing features 340.

In this way, in some examples, the one or more conductors 310 are routed to minimize, if not eliminate, stress concentrations, kink points, and other conditions detrimental to performance of the one or more conductors 310 and, in turn, the paddle lead 300, during a service life of the paddle lead 300. Also, in some examples, the one or more conductors 310 can be maintained away from other structures of the paddle lead 300, such as, for instance, other conductors 310 and/or the one or more electrodes 320, to decrease a chance of shorting between other structures and the one or more conductors 310.

With the one or more conductors 310 routed to the corresponding one or more electrodes 320, in some examples, the one or more distal ends of the one or more conductors 310 can be attached to the corresponding one or more electrodes 320. In some examples, the one or more conductors 310 are engaged with the corresponding one or more electrodes 320, for instance, by welding, brazing, or soldering the conductor 310 to the electrode 320. In some examples, where the one or more conductors 310 include one or more crimp tubes 312 at the one or more distal ends of the one or more conductors 310, the one or more crimp tubes 312 are engaged with the corresponding one or more electrodes 320, for instance, by welding, brazing, or soldering the crimp tube 312 to the electrode 320.

Figure 4F:
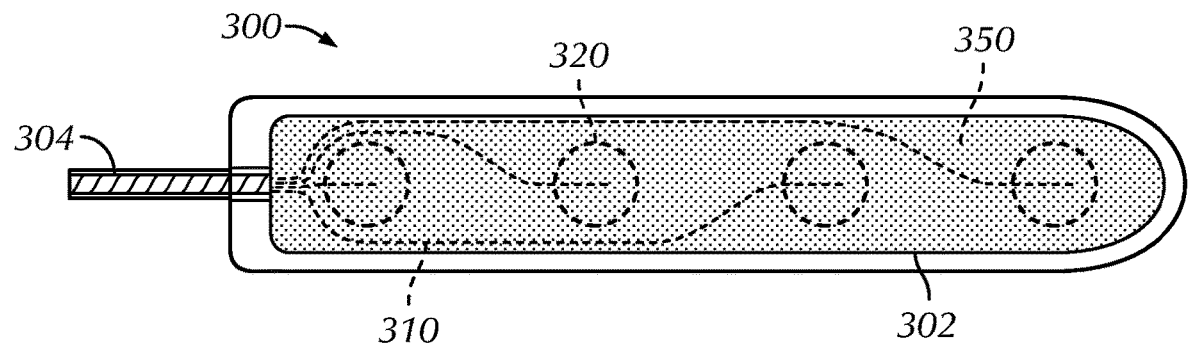

Referring now to FIG. 4F, in some examples, one or more other layers can be placed on and/or attached to the flexible substrate 330 or otherwise added to the paddle 302 of the paddle lead 300, depending on the function and performance requirements of the paddle lead 300. In some examples, a mesh layer 350 can be placed on the flexible substrate 330 to increase strength of the paddle 302 and reduce the chances of the paddle 302 tearing, ripping, or otherwise becoming compromised. In other examples, one or more other layers can be added to the paddle 302, in addition to or instead of, the mesh layer 350. Such additional layers, in some examples, can include multiple mesh layers. In other examples, no additional layers need be added, if performance requirements of the paddle lead 300 do not necessitate such additional layers.

In some examples, once the one or more conductors 310 are properly routed and constrained with respect to the flexible substrate 330 and any additional layers (for instance, the mesh layer 350) are added, the flexible substrate 330 is encapsulated with the one or more conductors 310 constrained and managed by the one or more routing features 340 to completely encase the one or more conductors 310.

Such encapsulation, in various examples, can include various additional processing, such as, but not limited to, overmolding, backfilling, potting, reflowing, and/or laminating. In some examples, such additional processing forms the paddle 302 and encapsulates the one or more conductors 310 within the paddle 302 in the proper shape, spacing, positioning, location, and/or orientation that was maintained during encapsulation and any additional processing using the one or more routing features 340, as described herein. In some examples, the material used for encapsulation is the same as the material of the flexible substrate 330. In other examples, the encapsulation material is different than the flexible substrate 330 material. In some examples, the one or more conductors 310 extend from the paddle 302 through the lead wire 304 for connection to a device (such as a stimulation, monitoring, and/or other device) at the proximal end of the lead wire 304.

Figure 5:
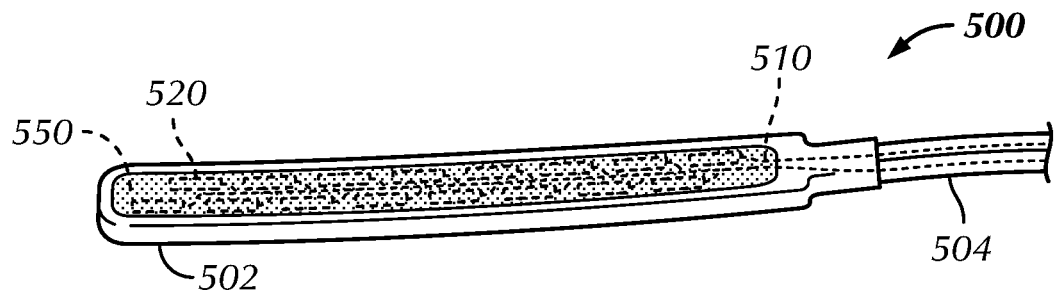
FIG. 5 is a perspective view of a medical device made using a conductor management method in accordance with at least one example of the invention.

Referring to FIG. 5, in some examples, the present inventive subject matter can be used within a medical device 500, such as a paddle lead 500. The paddle lead 500, in some examples, includes a paddle 502 at a distal end of the paddle lead 500, the paddle 502 being configured to be implanted within a patient for stimulation of tissue or other structures within the patient and/or monitoring of physiological parameters. In some examples, the paddle 502 includes one or more electrodes 520 to be positioned proximate the tissue or other structure in order to electrically stimulate the structure, measure properties of the structure, or the like. In some examples, the one or more electrodes 520 are exposed or extend at least slightly out of a surface of the paddle 502 to allow the one or more electrodes 520 to directly contact the tissue or other structure against which the paddle 502 is placed to allow for proper electrical stimulation of the tissue or other structure, physiological parameter measurement of the tissue or other structure, or the like. In some examples, the one or more electrodes 520 are electrically coupled to one or more conductors 510, which extend proximally into and through a lead wire 504 to a proximal device. The proximal device, in various examples, can include different types of devices, including, but not limited to, one or more of an implanted device, an external device, a stimulation device, a monitoring device, a drug-dispensing device, or the like.

In some examples, proper routing of the one or more conductors 510 within the paddle 502 is important to allow for proper electrical connections; inhibition, if not elimination, of potential electrical shorting; and proper layout and positioning of the one or more conductors 510 given the performance requirements of the paddle lead 500. In order to obtain such proper routing of the one or more conductors 510, in some examples, the one or more conductors 510 must be placed and maintained in the proper positions throughout formation and manufacture of the paddle lead 500. Various methods of conductor 510 management are described herein with respect to various medical devices, such as the paddle lead 500.

Initially, in some examples, the present method of conductor 510 management includes identifying the one or more routing features 540 on the flexible substrate 530 and understanding a planned conductor 510 arrangement, for instance, as detailed in a manufacturing procedure.

Referring now to FIGS. 6A-6G, in some examples, a method of conductor 510 management for a medical device, such as the paddle lead 500, is shown. In some examples, a flexible substrate 530 is provided, the flexible substrate 530 including at least one routing feature 540. The flexible substrate 530 can include the at least one electrode 520 disposed therein and/or thereon. In some examples, the flexible substrate 530 include at least one void 532 therein configured to accept the at least one electrode 520 within the void 532 when the at least one electrode 520 is to be affixed within the flexible substrate 530. The at least one electrode 520, in some examples, is located along the flexible substrate 530 in a proper position for the paddle lead 500 to allow the at least one electrode 520 to perform to electrically stimulate the tissue or other structure, measure the physiological parameter of the tissue or other structure, or the like.

In some examples, the at least one routing feature 540 is configured to anchor, route, and/or otherwise position the at least one conductor 510 within the paddle 502 of the paddle lead 500. In some examples, the at least one routing feature 540 is integrally formed with the flexible substrate 530. In some examples, the at least one routing feature 540 extends outwardly from a surface of the flexible substrate 530. In various examples, the routing feature 540 can include one or more of a rib, a bump, a protrusion, or the like, extending outwardly from the surface of the flexible substrate 530. In some examples, the flexible substrate 530 can include more than one routing feature 540, depending upon the number of conductors 510 that are to be used within the paddle lead 500 and the intended routing of the conductors 510 within the paddle 502. In such instances, the present method of conductor 510 management for a medical device, such as the paddle lead 500, can be repeated for each conductor 510 that is to be used within the paddle lead 500.

Figure 6A:
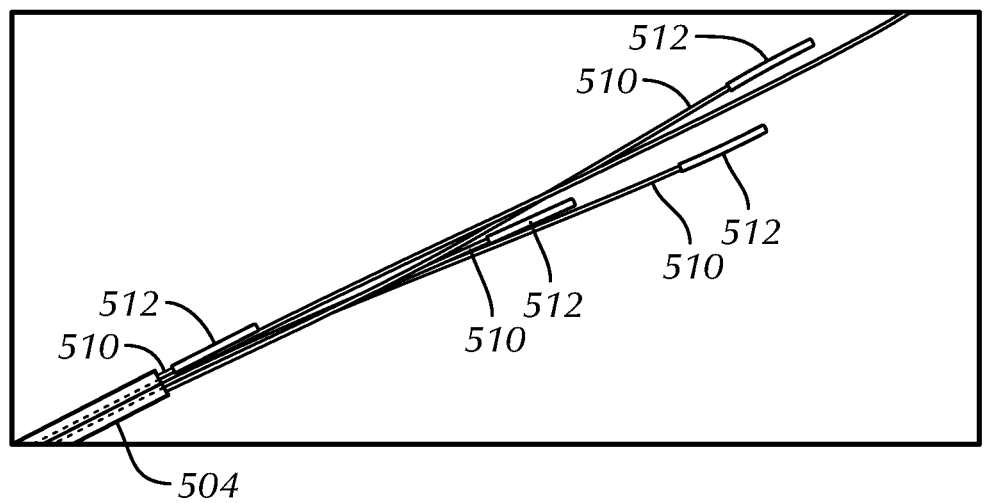
FIGS. 6A-6G are perspective views of steps of a conductor management method in accordance with at least one example of the invention.

Referring now to FIG. 6A, in some examples, one or more conductors 510 extend distally from within the lead wire 504 toward the flexible substrate 530 attached to a distal end of the lead wire 504. In some examples, the one or more conductors 510 can include coil or straight cable. In some examples, the one or more conductors 510 include a crimp tube 512 at the end of each of the one or more conductors 510. In other examples, the one or more conductors 510 do not include a crimp tube.

Figure 6B:
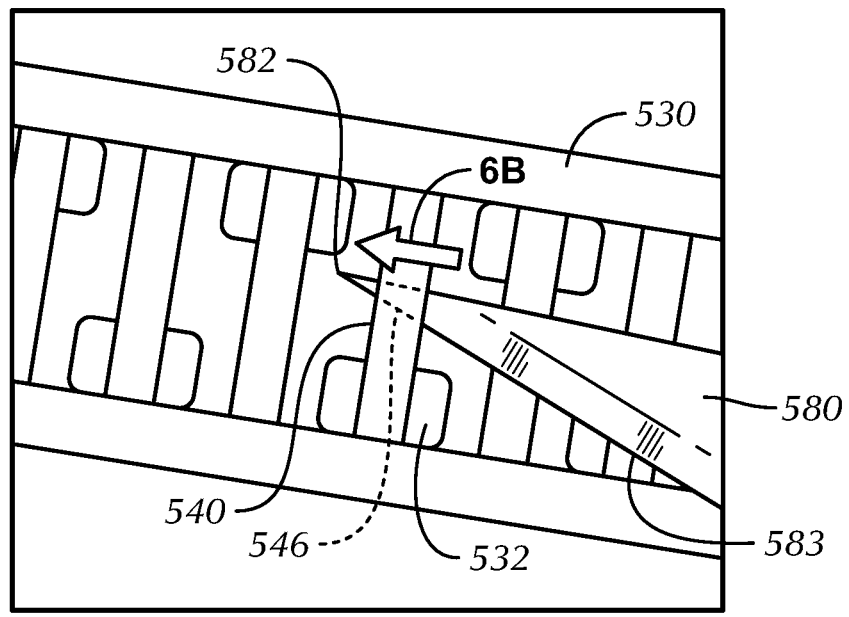
Figure 6C:
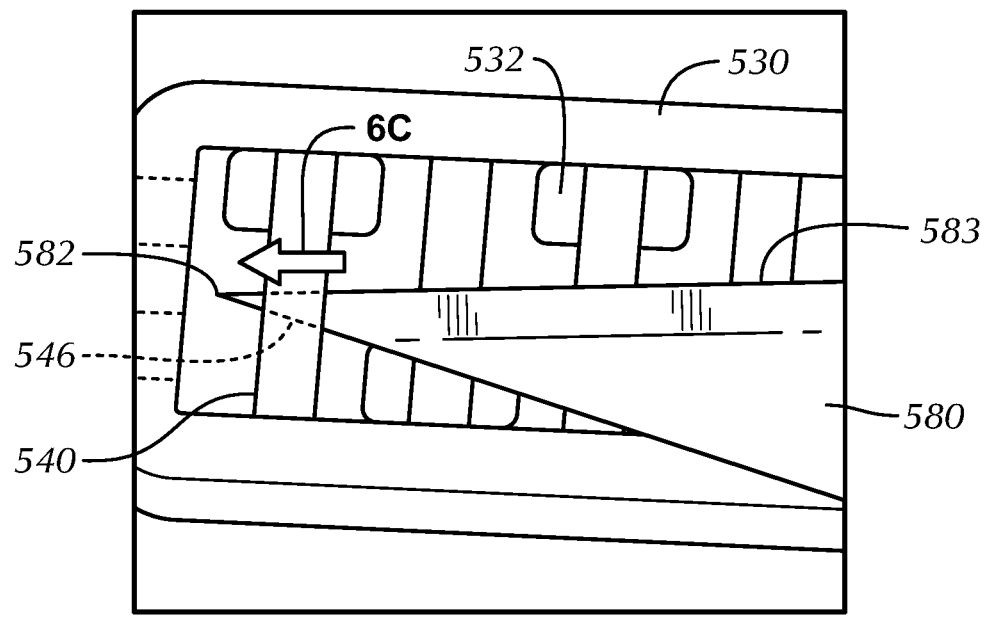

Referring to FIGS. 6B and 6C, in some examples, a hole 546 is cut in the at least one routing feature 540 using a cutting device 580. In some examples, the cutting device 580 includes a blade 580. In some examples, the blade 580 includes a scalpel or precision knife. In some examples, the blade 580 includes a distal tip 582 and a sharpened edge 583 configured to enable cutting of the at least one routing feature 540. In further examples, the distal tip 582 can include a sharpened tip to facilitate piercing of the at least one routing feature 540 with the blade 580, with the sharpened edge 583 of the blade 580 extending proximally from the distal tip 582. In some examples, the blade 580 is pushed through the routing feature 540 along arrow 6B, 6C. That is, in some examples, a user places the blade 580 at one side of the routing feature 540 and pushes the blade 580 along the arrow 6B, 6C through the routing feature 540 and out through the other side of the routing feature 540 to create the hole 546 through the routing feature 540. In some examples, a cutting direction is alternated for each routing feature, as is illustrated in FIG. 6B in which the sharpened edge 583 is facing down and in FIG. 6C in which the sharpened edge 583 is facing up. Although the cutting device 580 is described in some examples as being a blade 580, in other examples, other cutting devices can be used to form the hole 546 in the at least one routing feature 540, such as, but not limited to, a needle, a drill, a poker, a heated probe, a laser, and/or the like. In some examples, the hole 546 is disposed within the routing feature 540 in an intermediate portion of the routing feature 540 between the flexible substrate 530 and a top of the routing feature 540, such that there is material of the routing feature 540 both above and below the hole 546. In other examples, the hole can be formed at the top of the routing feature, such that the hole forms essentially a notch in the top of the routing feature. In still other examples, the hole can be formed at a bottom of the routing feature where the routing feature meets the flexible substrate.

Figure 6D:
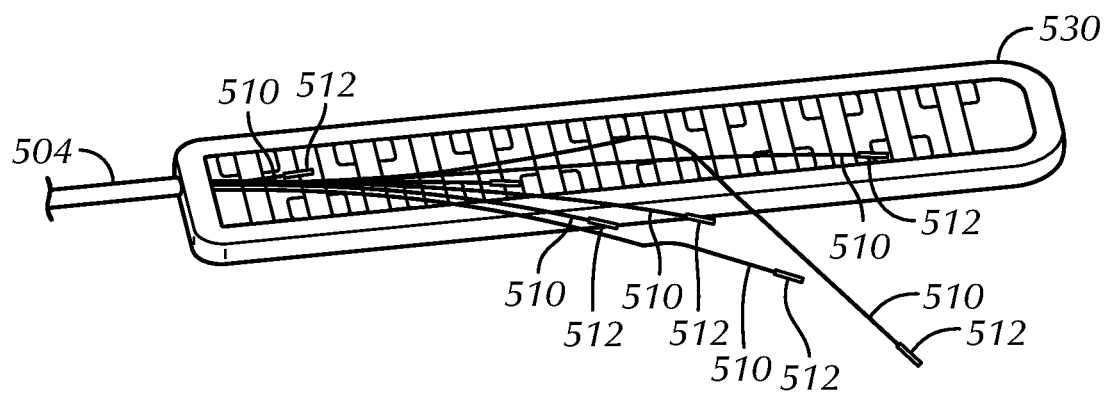

Referring to FIG. 6D, in some examples, the flexible substrate 530 is coupled to the lead wire 504 with the one or more conductors 510 extending distally out of the lead wire 504 and along the flexible substrate 530. In some examples, the number of conductors 510 corresponds to the number of electrodes 520. In further examples, the conductors 510 can be of lengths corresponding to the electrode 520 to which the conductor 510 is to be ultimately connected, with the conductors 510 extending to the more distally-located electrodes 520 being longer than the conductors 510 extending to the more proximally-located electrodes 520.

Figure 6E:
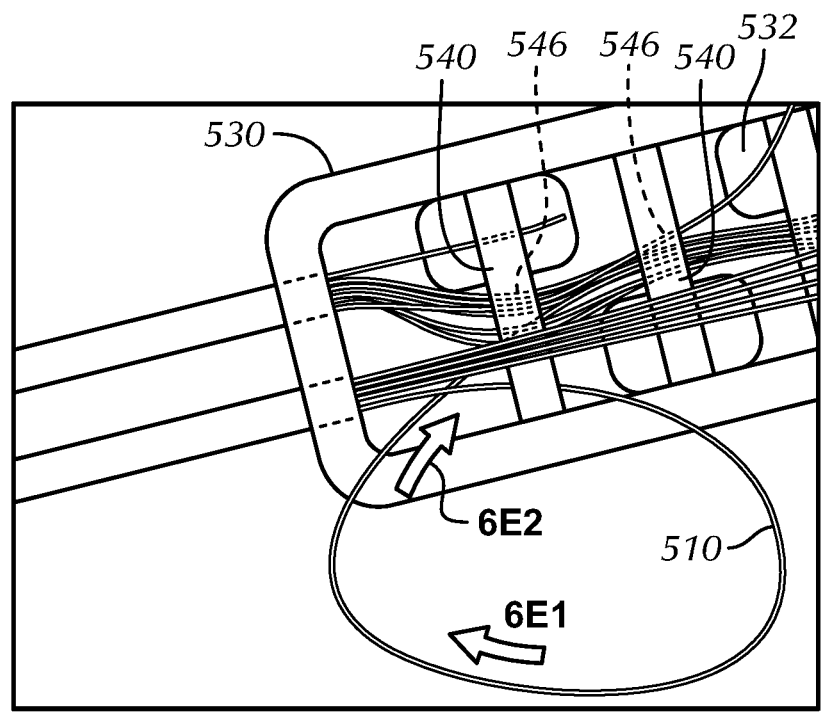

Referring now to FIG. 6E, in some examples, once the one or more holes 546 are formed in the one or more routing features 540, the one or more conductors 510 are passed through the one or more holes 546 in order to at least partially constrain the one or more conductors 510, thereby maintaining the orientation and position of the one or more conductors 510 with respect to the one or more routing features 540 and the flexible substrate 530. In this way, in some examples, the one or more routing features 540 act to maintain and manage positioning of the one or more conductors 510 within the medical device, such as, for instance, the paddle lead 500. As discussed above, the present method of conductor 510 management for a medical device, such as the paddle lead 500, is repeated for each conductor 510 of the paddle lead 500 until each conductor 510 is properly oriented, located, or otherwise positioned, using appropriate routing features 540 along a route of each conductor 510 in order to maintain such proper orientation, location, and/or positioning. In the present example, the paddle lead 500 includes sixteen conductors 510, so, once the sixteen conductors 510 are properly oriented, located, or otherwise positioned with respect to the flexible substrate 530, the electrodes 520, and each other, with the conductors 510 being maintained in place and constrained by being passed through the holes 546 in the routing features 540, further processing of the paddle lead 500 can be performed. In some examples, some holes 546 in some routing features 540 include more than one conductor 510 being routed therethrough in order to be routed to the proper electrode 520. In some examples, each conductor 510 is brought around along arrows 6E1, 6E2 to a proximal side of the proximal-most routing feature 540 and pushed through the hole 546 in the proximal-most routing feature 540 and then pushed through the holes 546 of each successively distal routing feature 540 until each conductor 510 reaches the electrode 520 to which the conductor 510 is to be attached. In some examples, the conductor 510 to be attached to the proximal-most electrode 520 need not be passed through any routing features 540 because it extends out from the lead wire 504 and straight to the electrode 520. In some examples, the crimp tubes 512 disposed at the distal ends of the conductors 510 stiffens the distal ends of the conductors 510, thereby facilitating the conductors 510 being pushed through the holes 546 of the routing features 540.

Figure 6F:
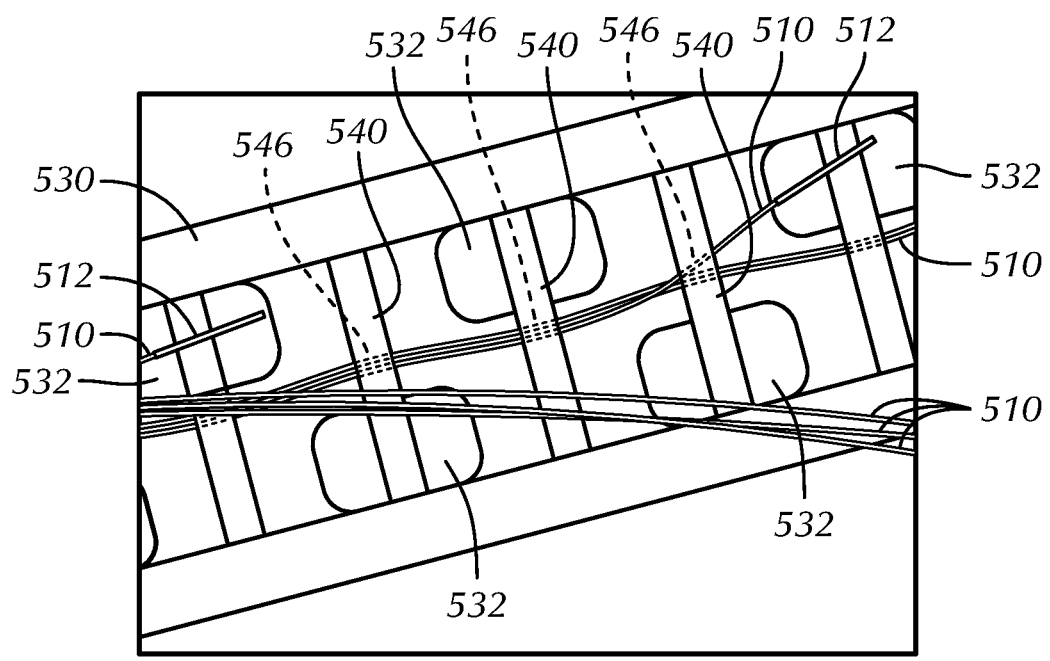
Figure 6G:
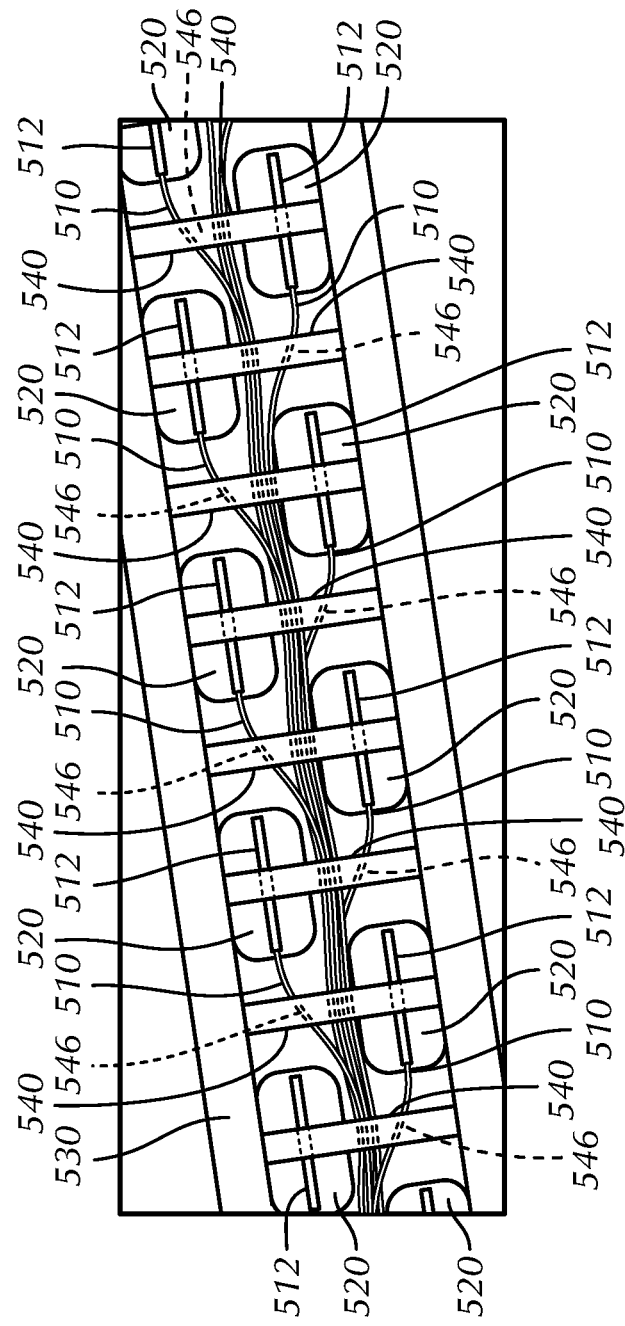

Referring now to FIGS. 6E-6G, the conductor 510 management method is repeated for each conductor 510, such that the conductors 510 are generally routed down a center of the flexible substrate 530 with each conductor 510 being split off to route to its respective electrode 520 when the conductor 510 gets to the electrode 520. Although this conductor 510 management and routing scheme is shown in the example of FIGS. 6E-6G, it should be understood that other conductor 510 management and routing schemes can be used depending upon the size and shape of the paddle 502, the number of conductors 510, the number and placement of the electrodes 520, and the purpose and performance requirements of the paddle lead 500. In some examples, once all of the one or more conductors 510 are routed through the proper routing features 540, any necessary final adjustments are made to finalize shape, spacing, positioning, location, and/or orientation of the one or more conductors 510. Such shape, spacing, positioning, location, and/or orientation of the one or more conductors 510 is maintained by the constraint offered by the at least one or more conductors 510 being routed through the one or more holes 546 in the one or more routing features 540.

In this way, in some examples, the one or more conductors 510 are routed to minimize, if not eliminate, stress concentrations, kink points, and other conditions detrimental to performance of the one or more conductors 510 and, in turn, the paddle lead 500, during a service life of the paddle lead 500. Also, in some examples, the one or more conductors 510 can be maintained away from other structures of the paddle lead 500, such as, for instance, other conductors 310 and/or the one or more electrodes 520, to decrease a chance of shorting between other structures and the one or more conductors 510.

With the one or more conductors 510 routed to the corresponding one or more electrodes 520, in some examples, the one or more distal ends of the one or more conductors 510 can be attached to the corresponding one or more electrodes 520. In some examples, the one or more conductors 510 are engaged with the corresponding one or more electrodes 520, for instance, by welding, brazing, or soldering the conductor 510 to the electrode 520. In some examples, where the one or more conductors 510 include one or more crimp tubes 512 at the one or more distal ends of the one or more conductors 510, the one or more crimp tubes 512 are engaged with the corresponding one or more electrodes 520, for instance, by welding, brazing, or soldering the crimp tube 512 to the electrode 520.

Referring again to FIG. 5, in some examples, one or more other layers can be placed on and/or attached to the flexible substrate 530 or otherwise added to the paddle 502 of the paddle lead 500, depending on the function and performance requirements of the paddle lead 500. In some examples, a mesh layer 550 can be placed on the flexible substrate 530 to increase strength of the paddle 502 and reduce the chances of the paddle 502 tearing, ripping, or otherwise becoming compromised. In other examples, one or more other layers can be added to the paddle 502, in addition to or instead of, the mesh layer 550. Such additional layers, in some examples, can include multiple mesh layers. In other examples, no additional layers need be added, if performance requirements of the paddle lead 500 do not necessitate such additional layers.

In some examples, once the one or more conductors 510 are properly routed and constrained with respect to the flexible substrate 530 and any additional layers (for instance, the mesh layer 550) are added, the flexible substrate 530 is encapsulated with the one or more conductors 510 constrained and managed by the one or more routing features 540 to completely encase the one or more conductors 510. Such encapsulation, in various examples, can include various additional processing, such as, but not limited to, overmolding, backfilling, potting, reflowing, and/or laminating. In some examples, such additional processing forms the paddle 502 and encapsulates the one or more conductors 510 within the paddle 502 in the proper shape, spacing, positioning, location, and/or orientation that was maintained during encapsulation and any additional processing using the one or more routing features 540, as described herein. In some examples, the material used for encapsulation is the same as the material of the flexible substrate 530. In other examples, the encapsulation material is different than the flexible substrate 530 material. In some examples, the one or more conductors 510 extend from the paddle 502 through the lead wire 504 for connection to a device (such as a stimulation, monitoring, and/or other device) at the proximal end of the lead wire 504.

Although various methods of conductor management are shown and described herein with respect to various medical devices, such as the cuff lead 100 and the paddle lead 300, 500, it is contemplated that the methods of conductor management can be used with other medical devices not specifically shown and described herein. For instance, in some examples, the present method of conductor management can be used to manage and route conductors within other types of leads, such as cylindrical leads.

In this way, in some examples, the present method of conductor 110, 310, 510 management provides for visual conductor 110, 310, 510 organization, which facilitates repeatable shape for conductor 110, 310, 510 strain relief and production uniformity. Also, in some examples, physical separation and control of conductors 110, 310, 510 is possible, thereby increasing isolation of channels and decreasing potential for current leakage across channels. Moreover, in some examples, the present method of conductor management provides for repeatable production of medical devices 100, 300, 500, with physical landmarks (routing features 140, 340, 540) placed onto the flexible substrate 130, 330, 530 to guide the manufacturing process. In some examples, the present inventive subject matter includes the medical devices 100, 300, 500 within which is included the conductor 110, 310, 510 management described herein.

The present inventors have recognized, among other things, that the present inventive subject matter can be used to provide conductor management within a medical device without increasing componentry, introducing potentially hazardous materials to the medical device, or requiring additional energy or processing. In various examples, the present inventive subject matter is advantageous in that it provides for conductor management without requiring additional components or bulk (adhesive, clips, coatings, etc.) in order to fasten, route, and/or otherwise position conductors within the medical device. In some examples, the present inventive subject matter advantageously provides for securing of conductors within the medical device regardless of insulation material type, finish, and/or thickness of the conductors. In some examples, the present inventive subject matter is advantageous in that it allows for physical landmarks to be placed onto a flexible substrate to guide the manufacturing process for repeatability, thereby decreasing, if not eliminating, the need for measuring locations of securing points and the possibility of misaligned securing points. While various advantages of the exemplary systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A method of conductor management within a medical device, the method comprising:
   providing a flexible substrate, the flexible substrate including at least one routing feature, the at least one routing feature including a protrusion extending outwardly from a surface of the flexible substrate;
   with a cutting device, cutting a hole in the at least one routing feature; and
   passing a conductor through the hole in the at least one routing feature, the routing feature acting to maintain and manage positioning of the conductor within the medical device.

2. The method of claim 1, wherein cutting the hole includes piercing the hole through the at least one routing feature using a needle.

3. The method of claim 2, wherein passing the conductor through the hole includes:

threading the conductor through a lumen of the needle with the needle disposed within the hole; and removing the needle from within the hole and over the conductor to leave the conductor within the hole of the at least one routing feature.

4. The method of claim 1, wherein cutting the hole includes cutting the hole through the at least one routing feature using a blade.

5. The method of claim 1, comprising encapsulating the flexible substrate with the conductor disposed within the hole in the at least one routing feature to completely encase the conductor.

6. The method of claim 1, comprising attaching the conductor to an electrode disposed within the flexible substrate.

7. The method of claim 1, wherein providing the flexible substrate includes the flexible substrate including two or more routing features disposed along the flexible substrate.

8. The method of claim 7, wherein cutting the hole in the at least one routing feature includes cutting a hole in each of the two or more routing features.

9. The method of claim 8, wherein passing the conductor through the hole in the at least one routing feature includes passing two or more conductors through the holes in the two or more routing features.

10. The method of claim 9, wherein passing the conductor through the hole in the at least one routing feature includes passing multiple conductors of the two or more conductors through at least one of the holes in the two or more routing features.

11. The method of claim 9, wherein passing the conductor through the hole in the at least one routing feature includes passing no more than one conductor of the two or more conductors through each of the holes in the two or more routing features.

12. The method of claim 1, wherein providing the flexible substrate includes providing the flexible substrate with the at least one routing feature being integrally formed with the flexible substrate.

13. A method of conductor management within a medical device, the method comprising:
providing a flexible substrate, the flexible substrate including a plurality of routing features disposed along the flexible substrate, the plurality of routing features each including a protrusion extending outwardly from a surface of the flexible substrate;
with a cutting device, cutting a hole in each of the plurality of routing features; and
passing a plurality of conductors through the holes in the plurality of routing features, the plurality of routing features acting to maintain and manage positioning of the plurality of conductors within the medical device.

14. The method of claim 13, wherein:
cutting the hole includes piercing the hole through at least one of the plurality of routing features using a needle; and
passing one of the plurality of conductors through at least one of the holes includes:
threading the conductor through a lumen of the needle with the needle disposed within the hole; and
removing the needle from within the hole and over the conductor to leave the conductor within the at least one hole.

15. The method of claim 13, wherein cutting the hole includes cutting the hole through at least one of the plurality of routing features using a blade.

16. The method of claim 13, comprising encapsulating the flexible substrate with the plurality of conductors disposed within the holes in the plurality of routing features to completely encase the plurality of conductors.

17. The method of claim 13, comprising attaching the plurality of conductors to a plurality of electrodes disposed within the flexible substrate.

18. The method of claim 13, wherein passing the plurality of conductors through the holes in the plurality of routing features includes passing multiple conductors of the plurality of conductors through at least one of the holes in the plurality of routing features.

19. The method of claim 13, wherein passing the plurality of conductors through the holes in the plurality of routing features includes passing no more than one conductor of the plurality of conductors through each of the holes in the plurality of routing features.

20. A method of conductor management within a medical device, the method comprising:
providing a flexible substrate, the flexible substrate including a plurality of routing features disposed along the flexible substrate, the plurality of routing features each including a protrusion extending outwardly from a surface of the flexible substrate and being integrally formed with the flexible substrate;
with a cutting device, cutting a hole in each of the plurality of routing features;
passing a plurality of conductors through the holes in the plurality of routing features, the plurality of routing features acting to maintain and manage positioning of the plurality of conductors within the medical device;
attaching the plurality of conductors to a plurality of electrodes disposed within the flexible substrate; and
encapsulating the flexible substrate with the plurality of conductors disposed within the holes in the plurality of routing features to completely encase the plurality of conductors.

* * * * *